(12) United States Patent
Amat Roldan et al.

(10) Patent No.: US 9,589,347 B2
(45) Date of Patent: Mar. 7, 2017

(54) COMPUTER IMPLEMENTED METHOD FOR ASSESSING VASCULAR NETWORKS FROM MEDICAL IMAGES AND USES THEREOF

(71) Applicants: EXPERT YMAGING, SL, Barcelona (ES); FUNDACIÓ CLINIC PER A LA RECERCA BIOMÉDICA (FCRB), Barcelona (ES); HOSPITAL CLINIC I PROVINCIAL DE BARCELONA, Barcelona (ES); UNIVERSITAT DE BARCELONA, Barcelona (ES); CENTRO DE INVESTIGACIÓN BIOMÉDICA EN RED DE ENFERMEDADES HEPÁTICAS Y DIGESTIVAS (CIBEREHD), Barcelona (ES)

(72) Inventors: Ivan Amat Roldan, Barcelona (ES); Jaime Bosch Genover, Barcelona (ES); Annalisa Berzigotti, Barcelona (ES); Maria Rosa Gilabert Solé, Sabadadell (ES)

(73) Assignees: EXPERT YMAGING, S.L., Barcelona (ES); HOSPITAL CLINIC I PROVINCIAL DE BARCELONA, Barcelona (ES); FUNDACIO CLINIC PER A LA RECERCA BIOMEDICA (FCRB), Barcelona (ES); UNIVERSITAT DE BARCELONA, Barcelona (ES)

( * ) Notice: Subject to any disclaimer, the term of this patent is extended or adjusted under 35 U.S.C. 154(b) by 0 days.

(21) Appl. No.: 14/779,000

(22) PCT Filed: Mar. 20, 2014

(86) PCT No.: PCT/IB2014/000392
§ 371 (c)(1),
(2) Date: Sep. 21, 2015

(87) PCT Pub. No.: WO2014/155174
PCT Pub. Date: Oct. 2, 2014

(65) Prior Publication Data
US 2016/0042514 A1    Feb. 11, 2016

(30) Foreign Application Priority Data
Mar. 28, 2013  (EP) .................................. 13001621

(51) Int. Cl.
*G06K 9/00*    (2006.01)
*G06T 7/00*    (2006.01)
(Continued)

(52) U.S. Cl.
CPC .......... *G06T 7/0016* (2013.01); *A61B 8/0891* (2013.01); *A61B 8/481* (2013.01);
(Continued)

(58) Field of Classification Search
None
See application file for complete search history.

(56) References Cited

U.S. PATENT DOCUMENTS 5,150,292 A * 9/1992 Hoffmann .............. A61B 6/481
250/303
2007/0165920 A1* 7/2007 Gering ................... A61B 5/055
382/128
(Continued)

FOREIGN PATENT DOCUMENTS

WO   WO 2011/293150 A1   5/2007
WO   WO 2014155174 A1   10/2014

OTHER PUBLICATIONS

Aylward et al ("Spatial Graphs for Intra-cranial vascular network characterization", 2005).*
(Continued)

*Primary Examiner* — Avinash Yentrapati

INPUT                                                                                   OUTPUT sequence functional connectivity mapper of vascular networks → vascular network model for specific organ/disease → risk factor

(74) *Attorney, Agent, or Firm* — Robert J. Hess; Hess Patent Law Firm

(57) ABSTRACT

The method comprising acquiring and analyzing by computer means image information of video sequences of two or more dimensions obtained from contrast-enhanced signals, for example ultrasound, coherence tomography, fluorescence images, or Magnetic Resonance Imaging, of a body part or tissue, for example of an organ, of a living subject; detecting events from said information of video sequences; selecting a Region of Interest of said body part or tissue; computing a first graph representative of a local vascular network of said image information of video sequences in which the edges of the graph are estimated by the temporal relationship among spatially remote signals of said image information of video sequences within a set of video sequences; and using said graph for assessment of vascular networks.

16 Claims, 2 Drawing Sheets

(51) Int. Cl.
*A61B 8/08* (2006.01)
*G06T 11/20* (2006.01)

(52) U.S. Cl.
CPC .. *G06T 11/206* (2013.01); *G06T 2207/10016* (2013.01); *G06T 2207/10096* (2013.01); *G06T 2207/10121* (2013.01); *G06T 2207/10132* (2013.01); *G06T 2207/20104* (2013.01); *G06T 2207/30024* (2013.01); *G06T 2207/30056* (2013.01); *G06T 2207/30101* (2013.01)

(56) References Cited

U.S. PATENT DOCUMENTS

| | | | | |
|---|---|---|---|---|
| 2010/0296709 | A1* | 11/2010 | Ostrovsky-Berman | G06T 7/0081 382/128 |
| 2011/0293150 | A1* | 12/2011 | Capolunghi | G06K 9/00 382/128 |
| 2012/0155725 | A1* | 6/2012 | Bathe | G06T 7/20 382/128 |
| 2014/0112562 | A1* | 4/2014 | Yamakawa | A61B 3/102 382/131 |
| 2015/0243023 | A1* | 8/2015 | Fan | G01R 33/4806 382/131 |
| 2015/0245776 | A1* | 9/2015 | Hirohata | A61B 6/032 600/504 |
| 2016/0019693 | A1* | 1/2016 | Silbersweig | G06T 7/0012 382/128 |

OTHER PUBLICATIONS

Aylward S.R. et al. "Spatial Graphs for Intra-cranial Vascular Network Characterization, Generation, and Discrimination", Jan. 2005 MIC CAI 2005 Lecture Notes in Computer Science; LNCS, Springer, Berlin DE Page)s) 59-6, XP019021692, ISBN: 978-3-540-29327-9.

Esneault S et al. "Graph Cut Liver Segmentation for Interstitial Ultrasound Therapy", 2007 Annual International Conference of the IEEE Aug. 22-26, 2007 [In conjunction with the biennial conference of the Society Francaise De Genie Biologique et Medical (SFGB, Aug. 22, 2007.

Siosteen A K et al: "Intra-operative uses of contrast-enhanced ultrasound", European Radiology Supplements, Springer, Berlin, DE vol. ISSN: 1613-3757m 001: 10.1007 /S10406-004-0081-6.

* cited by examiner

COMPUTER IMPLEMENTED METHOD FOR ASSESSING VASCULAR NETWORKS FROM MEDICAL IMAGES AND USES THEREOF

FIELD OF THE ART

The present invention generally relates to the field of imaging processing and information extraction applied to life sciences, and more particularly to a computer implemented method for assessing vascular networks from medical images by means of the analysis of medical images being enhanced by a contrast agent.

The invention further relates to the use of such method for monitoring patients, for example cirrhotic, or for monitoring of therapeutic effects for specific medical conditions.

PRIOR STATE OF THE ART

Several diseases produce changes to the local vascular system or perfusion of a body part and techniques that are able to measure such changes are an intensive field of research as they have the potential to become useful tools for many clinical applications. Different imaging techniques (including contrast-enhanced computerized tomography, CECT, contrast-enhanced magnetic resonance imaging, CE-MRI, and contrast enhanced ultrasound, CEUS) have been used to assess regional perfusion in different organs in healthy and diseased state (ischemic stroke; myocardial infarction) providing useful surrogates of clinical events. Even if technological advances have allowed detailed study of cerebral and cardiac perfusion by these imaging methods, several unmet needs remain for assessing the characteristics and changes in local vascularization in other organs and tissues, and in particular in the liver and in solid tumours due to their specific perfusion features.

Among the above mentioned imaging techniques, contrast-enhanced ultrasound has gained increasing consensus due to its low cost and easy access. For example, a set of guidelines for the use of contrast enhanced ultrasound (CEUS) was published in 2004 regarding liver applications for patient management. Then, a second edition of the guidelines in 2008 reflected changes in the available contrast agents and updated the guidelines for the liver, as well as implementing some non-liver applications like kidney, urethra, abdomen, prostate, pancreas, brain, heart and others [Claudon, 2008]. Further guidelines were then published in additional non-liver applications [Piscaglia, 2011] that refined previous guidelines and included non-reported applications in previous guidelines like paediatric, gastrointestinal tract, spleen, scrotum, lung, vascular, inflammatory joint diseases, tumour response treatment, breast, adrenal, gynaecology, perineum, urinary bladder, transplanted kidney, prostate cancer, aorto-caval fistula, free tissue transplants, extrahepatic biliary system, patients with renal failure and others. Recently, another update has been published to report more detailed liver indications [Claudon, 2013]. Therefore, utilization of CEUS in order to assess some properties of local vascular system or perfusion has seen an increased number of applications after it firstly appeared for liver applications. Therefore, the main description and scope within this document will be related to liver disease but this methodologies can be readily transferred to other pathologic conditions or clinical needs reported in the mentioned guidelines or related to assessment of vasculature system or perfusion of tissue, organ or body part. In addition, current utilization of CEUS information is limited as it requires manual, intensive and subjective interpretation of data with reduced objective criteria. Therefore, a more quantitative approach would increase the feasibility of CEUS in clinical practice.

Chronic liver diseases (CLD) are an example of the current complexity of patient management that would be favoured by the inclusion of patient-specific risk factor that requires less invasive clinical tests. In chronic liver diseases chronic injury to the liver (viruses, alcohol, autoimmunity, etc.) is followed by inflammation fibrosis (scarring related with collagen deposition) which progressively modify the normal liver anatomy and eventually impairs the liver function. The term "cirrhosis" identifies the final stage of chronic liver diseases, and is characterized by extensive fibrosis septa, regenerative nodules formation and vascular derangement. Cirrhosis appearance is a hallmark in the natural history of CLD, since it marks a brisk increase in the risk of primary liver cancer (hepatocellular carcinoma), and identifies patients at risk of developing portal hypertension (increased pressure gradient across the liver), which is the major pathophysiological factor for liver-related complications, that often lead to hospital admission, mortality or liver transplantation. Therefore, once cirrhosis has been detected it is crucial to stratify the individual patient's risk of having portal hypertension, developing complications and death, since this allows choosing the best available treatment taking into account treatment-related risks, benefits and cost-effectiveness.

Current techniques for liver evaluation are either highly invasive and cannot be performed routinely or lack sufficient sensitivity for the management of these patients.

Hepatic venous pressure gradient (HVPG) is the reference method to estimate portal hypertension; is obtained by hepatic vein catheterization and is considered the best surrogate marker of clinical events in hepatology. This technique is very reproducible and provides unique objective, numerical information on the severity of portal hypertension and has been correlated with histological severity of liver fibrosis. In addition, the HVPG is the only technique allowing testing the response to medical treatment of portal hypertension. Hepatic vein catheterization is moderately invasive, carries a modest discomfort and lasts between 20 and 120 minutes; complications are infrequent (<1% of cases). However, it is expensive, requires specific equipment and highly specialized personnel, and it is not available in all hospitals; this prevents its routine clinical use for monitoring and risk stratification. Therefore, non-invasive methods able to supply similar prognostic information are highly needed and have been actively investigated.

Laboratory tests, based on albumin, bilirubin, INR or their combination in the Child-Pugh and in the MELD scores, and platelet count correlate with the HVPG. The strength of these correlations is only moderate and does not allow a precise estimation of the HVPG; moreover, the accuracy of laboratory tests for diagnosing clinically significant portal hypertension is far from being ideal, and does not exceed 60-70%.

Elastography, and more specifically transient elastography (TE), is a well validated technique for the non-invasive assessment of liver fibrosis. Measurements are performed with an ultrasound transducer built on the axis of a vibrator; a vibration of mild amplitude and low frequency is transmitted, inducing a wave that propagates through the liver tissue, and pulse-echo acquisitions are performed to measure the velocity of propagation of the wave, which is directly related to tissue stiffness. Since fibrosis is the main determinant of tissue stiffness and of hepatic resistance to portal blood flow (the major determinant of portal pressure in early stages of portal hypertension), TE has been tested in recent years as a novel way of obtaining numerical, objective and operator-independent non-invasive surrogate data of HVPG. However, TE only differentiates between cirrhotic patients at low risk that do not require monitoring and patients at risk (when HVPG>12 mmHg) having a moderate impact in clinical managing of cirrhotic patients. In patients with values of HVPG>12 mmHg the correlation of TE with the HVPG is unsatisfactory. Hence, TE does not allow further stratifying the risk of patients with portal hypertension. In addition, major technical limitations of TE include the lack of visualization of the parenchyma in the region of interest, and failure to obtain any measurement or unreliable results in 3-16% of cases due to obesity or ascites. Therefore, techniques with high correlation to HVPG above 12 mmHg are currently needed.

Ultrasound (US) is a safe, cheap and repeatable imaging technique, which allows a real-time examination of the abdominal organs and large vessels; it is widely used in patients with cirrhosis for screening for hepatocellular carcinoma and features of portal hypertension. These approach has several limitations and it is not accurate enough [refs]. For example, its limitation of the technique depends upon the lack of visualization of parenchymal microvessels, which are those supporting the effective perfusion of hepatocytes, so maintaining tissue integrity and normal function.

Contrast Enhanced Ultrasound (CEUS) was a major advance in ultrasound imaging by introducing contrast media in the form of injectable tracers whose passage can be detected in the blood. It has been demonstrated that there is a linear relation between the microbubble concentration and the signal intensity on ultrasound, so time-intensity curves reflect the dynamics of microbubbles in vivo. Images are recorded and quantitative analysis of time-intensity curves of microbubbles is performed with specific software. This software uses raw linear ultrasound data to calculate indexes related with the velocity of blood flow and blood volume in the region of interest (ROI). Tracking software can be used to correct for breathing movement. Main functional indices usually determined after a single i.v. bolus are mean transit time, indices of blood volume (peak intensity, area under the curve—AUC, area under the wash-in and area under the wash-out) and indices of blood flow (time to peak intensity; slope of wash-in and time to peak intensity). CEUS has been endorsed by the European Medical Oncology Society to assess response to biological therapy for gastro-intestinal stromal tumours.

The rupture-reperfusion technique by CEUS also allows studying microbubbles kinetics. In this technique a continuous i.v. infusion of microbubbles is used to reach a saturated steady state blood concentration of microbubbles. Then, microbubbles are destroyed by a high mechanical index pulse of echoes in the organ under investigation, and the reperfusion of the organ by microbubbles is recorded and analysed. This technique has the advantage of allowing estimation of regional perfusion in solid organs (liver, myocardium, kidney, brain, etc.). Previous investigations by Bosch and co-workers confirmed that it can be used with success to assess regional hepatic perfusion (RHP) in healthy subjects and in patients with cirrhosis (Berzigotti, 2011). As expected, in cirrhosis RHP correlated with the severity of liver failure and portal hypertension.

However, the results of this technique in liver assessment are limited by the skills of the medical expert and the prognostic value or capability to stratify the risk of a patient is highly limited. This technique requires an extensive off-line processing of the video images that requires, for example, manual selection of frames and local positioning of a region of interest in which the average intensity for each frame is computed by software. Then, non-stationary dynamics of the intensity curve (like time to peak intensity or slope) have shown correlation to pathological status. However, this technique did not fulfil clinical needs; for instance, it did not appear reliable enough to mirror HVPG and changes in HVPG due to pharmacological therapy. This is a major limitation of all the known non-invasive techniques (including all imaging techniques) used to evaluate portal hypertension up to date. Obviously a more automated and accurate method is required to overcome the current limitations of non-invasive methods and to avoid the invasive measurement of HVPG.

SUMMARY OF THE INVENTION

Current state of the art proposals don't allow the analysis of video sequence of ultrasound images (2D/3D) to assess the complexity of the local vascular tree into a graph model. Therefore, an object of the invention is to provide a solution that analyzes said set of video sequences for further computing patient specific risk factors in the clinics.

To that end, according to a first aspect, the present invention provides a computer implemented method for assessing vascular networks from medical images, comprising as commonly in the art acquiring and analysing by computer means image information of video sequences of two or more dimensions obtained from contrast-enhanced signals, for example ultrasound, coherence tomography, fluorescence images, or Magnetic Resonance Imaging, of a body part or tissue, for example of an organ, of a living subject.

On contrary of the known proposals, and in a characteristic manner, the computed implemented method involves executing the following steps:
  detecting events from said information of video sequences;
  selecting a region of interest of said body part or tissue;
  computing a first graph representative of a local vascular network of said image information of video sequences in which the edges of the graph are estimated by the temporal relationship among spatially remote signals of said image information of video sequences within a set of video sequences; and
  using said graph for assessment of vascular networks.

Preferably, according to an embodiment, the assessment of the vascular networks comprises the computation of a specific risk factor of the living subject, organ or tissue by using a set of graph features of said first computed graph vascular network according to a predictive model of disease.

According to another embodiment, the detection of the events is performed when said image information of video sequences are acquired and analysed.

Preferably the predictive model of disease is a computer model, a statistical model, a data model, a graphical model, a decision model or system model. Or in an alternative, a general linear model, a support vector machine regression model, a random forest, a decision tree, a generative model, a discriminative model.

The first computed graph representative of a local vascular network further comprises: compensating the motion and deformation of the body part when performing said acquiring and analysing and compensating said acquired and analysed image information of video sequences.

In an alternative, the step of compensating the motion and deformation of said body part or tissue can be computed by means of a spatial compensation strategy such as a Speckle Tracking Echocardiography, a non-rigid registration, a rigid registration, a block matching, a local measure of similarity or a global measure of similarity. Or in yet another alternative, by means of an intensity compensation strategy such as an acoustic wave propagation model, a local equalization of the image information, a global equalization of the image information or image normalization with respect to echodensity of specific anatomical landmarks.

The specific risk factor of the living subject is computed by integrating information of at least one additional second and different computed graph corresponding to information of two different regions of the body part. Furthermore, the specific risk factor of the living subject still further comprises and additional step of computing graph measures of said computed graph to obtain a reduced set of features. These set of reduced features are preferably computed by at least one of the following approaches:
  a standard graph analysis using one or more of the following criteria, clustering coefficient, path length, global efficiency, local efficiency, small-wordless, degree or degree distribution,
  a spectral graph analysis using any of the following criteria, characteristic polynomial, eigenvalues, or eigenvectors.
  a power graph analysis using any of the following criteria, decomposition of graph in power graphs and power nodes, minimal power graphs, power graph greedy algorithm or modular graph decomposition;
  a hierarchical graph analysis using any of the following criteria, ordering by nested sets, hierarchical hidden Markov model, hierarchical clustering or hierarchical Bayes.

Preferably, according to another embodiment, the selection of the region of interest of the body part is done according to the following criteria:
  a) introduced through a user interface;
  b) automatically estimated by a specific algorithm to select regions of interest;
  c) automatically estimated in those regions in which absolute value of pixel variation is maximal before and after said event of step a);
  d) automatically estimated in those regions in which absolute value pixel variation is above a specific threshold before and after the event;
  e) automatically estimated at an arbitrary position of a transducer;
  f) a weighted combination of said steps c), d) and e); or
  g) adjusted through a user interface.

The estimation of the temporal relationship among spatially remote signals of the image information of video sequences within a set of video sequences can be computed either by computing a model-based approach by means of a statistical parametric mapping (SPM), a cross-correlation analysis (CCA); a coherence analysis (CA); or a predefined temporal model of local vessels or by computing a model-free approach by means of a modular graph decomposition or a clustering.

If the model-free approach is computed by means of the modular graph, this graph can be executed in an alternative by means of a principal component analysis or a singular value decomposition or by means of an independent component analysis (ICA). On contrary, if the model-free approach is computed by a clustering, said clustering can be performed in another alternative by means of a Fuzzy Clustering Analysis or an Hierarchical Clustering Analysis.

The data information used for computing the specific risk factor from said predictive model of disease can be for instance biochemical, elastographic, imaging, clinical, genetic, epigenetic, protein expression or folding or current scores data information regarding said living subject.

Finally, the method according to yet another embodiment computes the specific risk factor from said predictive model of disease by a complex biology system the input of which is done by parameters of the graph analysis selected among cellular automatons, a complex adaptive system, physiology simulators, and models of vascular patterns or others.

The invention, according to a second aspect, provides a use of the computer implemented method of the first aspect for monitoring cirrhotic patients of the liver of any etiology or other chronic liver diseases and their consequences. Furthermore, it provides a use of the computer implemented method of the first aspect for monitoring of therapeutic effects for specific medical conditions, such as oncology, prognosis, differentiation of healthy and abnormal tissue, such as development of tumours or assessment of response to anti-tumour therapy and for diagnosing abnormal vascularization or tumors.

BRIEF DESCRIPTION OF THE DRAWINGS

The previous and other advantages and features will be more fully understood from the following detailed description of embodiments, with reference to the attached, which must be considered in an illustrative and non-limiting manner, in which.

DETAILED DESCRIPTION OF SEVERAL EMBODIMENTS

Figure 1:
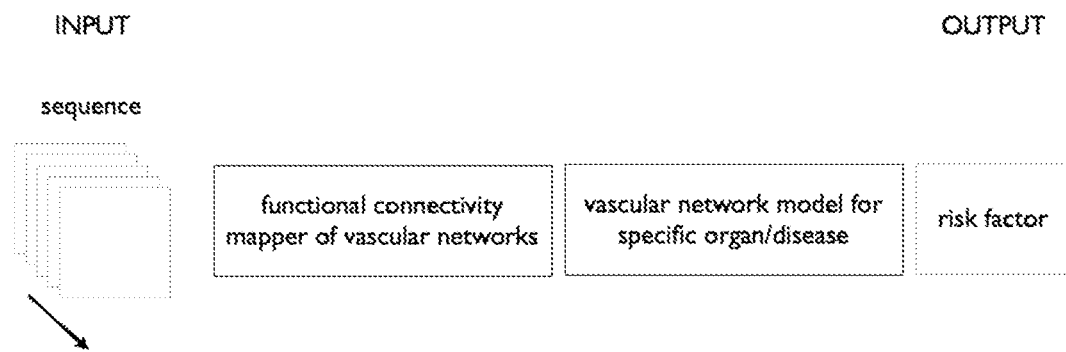
FIG. 1 is a schematic representation of the processing blocks that enable to compute patient specific risk factor used by the method of the present invention.

FIG. 1 shows the number of processing blocks: functional connectivity mapper of vascular networks and vascular network model for specific organ/disease, that enable to compute patient specific risk factor, according to the first aspect of the present invention.

Figure 2:
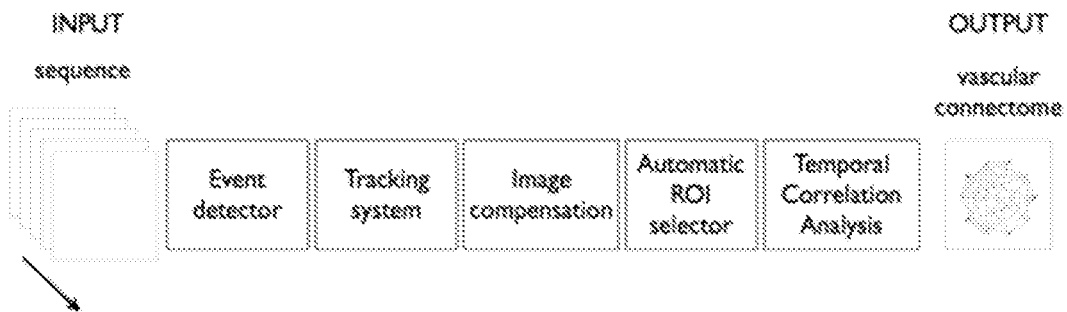
FIG. 2 is an example of the functional connectivity mapper of vascular networks (first block of FIG. 1) used by the method of the present invention.

FIG. 2 shows in an embodiment, the blocks included in the functional connectivity mapper of vascular network block of FIG. 1. These blocks are: an Event detector, a Tracking system, Image compensation, Automatic ROI detection and a Temporal Correlation Analysis.

Some characterizations of the main blocks used by the proposed invention will be described in the following paragraphs in order to better explain their functions, thus allowing the analysis of the set of video sequences for further computing patient specific risk factors in the clinics.

The Event detector module is a group of signal processing techniques that detects from time series when a specific event has occurred. These approaches require time series analysis and might involve for example direct thresholding of a temporal signal, detection of specific frequency components within a time interval, or feedback loops. On another hand, the tracking system module is a group of image processing techniques that estimates and compensates motion and deformation of tissue. These can be achieved by classical video tracking strategies as blob tracking, kernel-based tracking, contour tracking, feature matching, Kalman filter, particle filter.

Image registration is one of the most common approaches for feature matching and there exist different implementations having the following elements in common: source image, target image, similarity, optimization, transformation model, and transformed image. Source image is the initial image that will be registered (alignment plus deformation) to fit the target image. This procedure is generally iterative and will produce a number of transformed images in each iteration that will be assigned to the source image in the next iteration. There are a number of distinctive characteristics for different registration procedures: (1) intensity vs. feature based, (2) transformation models rigid or non-rigid, and local (i.e. block matching) or global, (3) common examples of image similarity measures include normalized or non-normalized cross-correlation, mutual information, sum of squared intensity differences, and ratio image uniformity, (4) standard examples of optimization strategies by gradient descent, downhill descent, Powell's. Among these strategies, specific developments have evolved towards Speckle Tracking Echocardiography (STE) as a preferred technique for video registration for ultrasound as it takes advantage of the interferometric patterns naturally produced in ultrasound imaging to estimate the local motion and deformation of tissue by tracking such interferometric patterns. These interferometric patterns, also named as "speckles" (a term borrowed from the optics field), are tracked consecutively frame to frame and ultimately resolved into angle-independent two-dimensional (2D) and three-dimensional strain-based sequences (3D). These sequences provide both quantitative and qualitative information regarding tissue deformation and motion of high interest for cardiology applications. Currently, the applications of STE are increasingly recognized. Strain results derived from STE have been validated using sonomicrometry and tagged MRI and results correlate significantly with tissue Doppler-derived measurements. For the proposed body part or tissue application, such as for the liver, the motion and deformation is known to be much smaller compared to heart beating. Therefore, these techniques will be directly implemented and no major problems are expected.

Image compensation is a processing step to remove noise and distortion artifacts from image acquisition, which are particularly evident in ultrasound propagation. These include an acoustic wave propagation model, a local equalization of the image information, and a global equalization of the image information or image normalization with respect to echodensity of specific anatomical landmarks.

Temporal Correlation Analysis or estimation of functional connectivity by time series analysis is a group of image processing techniques highly developed in the field of brain imaging to estimate the "temporal correlations between spatially remote (neuro) physiological events". In brain imaging, the contrast mechanism to estimate local brain activity is the changes in blood oxygen level dependent (BOLD) signal. In a similar manner, CE-US provides functional information about the local perfusion of a body part, such as the liver. In order to estimate the "temporal correlations among spatially remote events" there are a wide range of methods for the analysis of the video sequences, and these can be mainly classified in two main categories: model-based methods (statistical parametric mapping, cross-correlation, coherence) and model-free methods (PCA, ICA, clustering). Any of these approaches will enable the computation of a connectivity matrix, and thus, represent the local vascular network in the form of a graph model.

Figure 3:
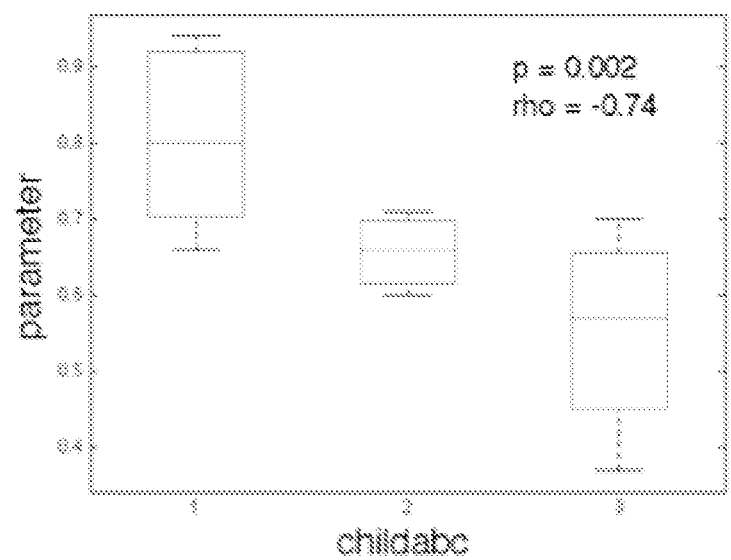
FIG. 3 is a representation of the correlation of the risk stratification (childabc) versus clustering (parameter) in a clinical study.
Figure 4:
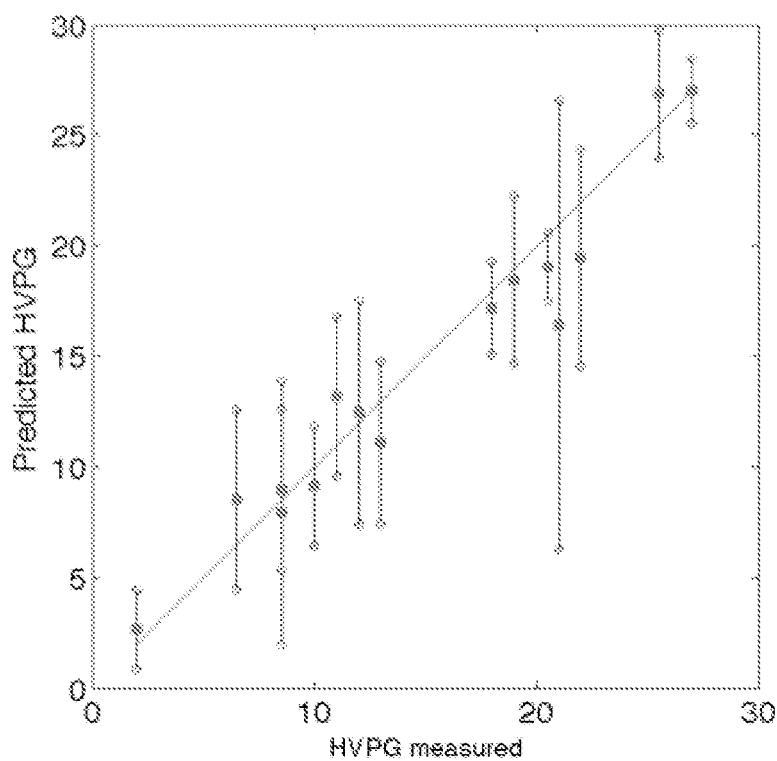
FIG. 4 is a representation of the cross validation of the HVPG measured invasively versus the predicted HVPG from CE_US video sequence with the proposed method of the present invention.

Concerning the graph analysis, there exist clear evidences that even simple graph parameters are associated to complex biology systems. Most remarkably, different studies have shown how such graph parameters computed from functional and structural brain networks are correlated with clinical end-points. For example, network efficiency has been related to multiple sclerosis patients with greater white matter lesion load and nodal degree to Alzheimer's patients with greater severity of local amyloid deposition. Other graph descriptors have been studied. To measure the node's hubness, a common, basic measure is the degree and, based on it, the degree distribution, which represents the whole brain graph. However, more elaborated measures of centrality can be used, such as betweenness centrality, closeness centrality, eigenvector centrality or edge centrality. Two basic measures evaluate efficiency of information transfer in a graph: the clustering coefficient and the path length, whose combination provides the small-world scalar. In turn, modularity of a brain network has been estimated through measures such as the intramodular degree or the participation coefficient. Nevertheless, it is necessary to extend this set of measures to account for other graph attributes and confirm whether this approach can be successfully implemented in other clinical applications, like the characterization of vascular networks of the liver. FIG. 3 and FIG. 4 show that healthy and cirrhotic patients exhibit significantly different vascular network parameters. This way, spectral graph analysis, leading to the algebraic connectivity descriptor; power graph analysis, introducing cliques, bicliques and starts; or modular graph decomposition, using graphs subsets of vertices called modules, should be included in this proposal. Hierarchical graph analysis might help to soundly define the most informative vascular graph within the hierarchy and to robustly estimate the graph descriptors. Additionally, longitudinal acquisitions of the patient will be acquired on different liver regions and therefore this represents a challenge in terms of integrating information of two different graphs, with different nodes and edges. This approach leads to multiple graph models for the same individual which must be hierarchically related. This idea is connected to the concept of hierarchical modularity or nested arrangement of modules within modules. It seems, therefore, natural to extend this concept and propose a procedure to reach a common graph that tracks along time and enables comprehensive comparison of an individual within different time points.

The Predictive Models for disease CE-US time series include an outrageous amount of data and many concepts of the graph analysis that are difficult to interpret as such are coded in an unfamiliar manner to a medical expert; similarly, engineers in charge of the imaging and post-processing do not understand many aspects of clinical practice. Predictive models of disease are built to translate, whenever is possible, such complex data into quantitative parameters that have been reported to relate to a specific biological process or physiological status. These parameters can be then statistically interpreted according to clinical context of the patient by a medical expert. More particularly, imaging biomarkers are a specific type of Predictive models of disease that extract most part of the information from images.

To improve the management of hypertensive cirrhotic patients, new quantitative CE-US imaging biomarkers are required. In this context, post-processing of CE-US can provide measures of the derangement of the hepatic vascular network and report on specific distortions like vascular occlusion, fibrosis, nodule formation and angiogenesis ("mechanical component") related with chronic liver damage and different impact on graph calculations. Functional vascular connectivity based on CE-US provides non-invasive measures of hepatic vascular networks properties and abnormalities.

In reference to FIGS. 1 and 2 it is described an exemplary embodiment of the proposed method. From those Figures, it is showed how graph measures can be directly correlated to HVPG or risk stratification. This embodiment includes a scheme that computes the graph model by the following steps: detecting with the event detector the disruption of microbubbles and starting the replenishment; computing by the tracking system the motion and deformation by block matching; compensating the video by correcting each frame according to the averaged video image prior to microbubble disruption; centering the region of interest, either manually or automatically, at the most dark region of the US image and closer to its centre; estimating the temporal relationship among spatially remote signals by computing the cross-correlation among times series of all data points, and computing the subsequent binarization of the adjacent matrix by thresholding the cross-correlation above a 0.5 factor. Then the clustering coefficient is computed from the binary matrix and the equivalent random network. The ratio of the two values is equivalent to normalized cluster coefficient. The predictive model of disease is built by the inverse of the normalized cluster coefficient as follows:

$$\hat{y}_i = C_i^{(r)}/C_i$$

where $\hat{y}_i$ is the predicted value of the model of disease for the subject i, $C_i^{(r)}$ is the average clustering coefficient of the equivalent random network of the matrix i, and $C_i$ is the average clustering coefficient of the matrix i. This predictive model of disease shows significant correlation to childabc parameter (for risk stratification) as shown in FIG. 3.

A second exemplary embodiment computes the graph model in the same manner to the first exemplary embodiment but in this case, the predictive model of disease is more complex. The input parameters of the predictive model of disease are substituted by a vector that contains the normalized distribution of the normalized clustering coefficient of all the network nodes. The computational model is trained according to data by principal components decomposition where three first components are kept and a random forest of the regression trees fits the data to the HVPG, measured values. FIG. 4 shows the predicted values of the model of disease for measured HVPG (current gold standard to assess risk of patients with cirrhosis) from out-of-bag data. Analogously, other fields of application are monitoring of therapeutic effects (i.e. oncology treatments), prognosis, and differentiation of healthy and abnormal tissue (i.e. tumours).

The invention claimed is:

1. A computer implemented method for assessing vascular networks from medical images, comprising:
   acquiring and analyzing by computer means image information of video sequences of two or more dimensions obtained from contrast-enhanced signals of a body part, organ or tissue of a living subject;
   detecting events from said image information of video sequences;
   selecting a region of interest of said body part, organ or tissue;
   computing a graph representative of a local vascular network of said image information of video sequences in which edges of the graph are estimated by the temporal relationship among spatially remote signals of said image information of video sequences within a set of video sequences; and
   using said graph for assessment of vascular networks.

2. The method according to claim 1, wherein said assessment of vascular networks comprises computation of a specific risk factor of said body part, organ or tissue by using a set of graph features of said computed graph representative of the local vascular network according to a predictive model of disease.

3. The method according to claim 1, wherein said detecting of events is performed when said image information of video sequences are acquired and analyzed.

4. The method according to claim 1, wherein said computing of said first graph representative of a local vascular network further comprises the following steps:
   compensating motion and deformation of said body part, organ or tissue when performing said acquiring and analyzing; and
   compensating said acquired and analyzed image information of video sequences.

5. The method according to claim 1, further comprising:
   computing graph measures of said computed graphs to obtain a reduced set of features.

6. The method according to claim 4, wherein said step of compensating the motion and deformation of said body part, organ or tissue is computed by means of a spatial compensation strategy by at least one selection from the group consisting of a speckle tracking echocardiography, a non-rigid registration, a rigid registration, a block matching, a local measure of similarity and a global measure of similarity.

7. The method according to claim 4, wherein said step of compensating said acquired and analyzed image information of video sequences of said body part, organ or tissue is computed by means of an intensity compensation strategy by at least one selection from the group consisting of an acoustic wave propagation model, a local equalization of the image information, a global equalization of the image information and an image normalization with respect to echodensity of specific anatomical landmarks.

8. The method according to claim 1, wherein said region of interest of the body part, organ or tissue is selected by at least one of the following criteria selected from the group consisting of:
   a) introduced through a user interface;
   b) automatically estimated by a specific algorithm to select Regions Of Interest;
   c) automatically estimated in those regions in which absolute value of pixel variation is maximal before and after said event is detected;
   d) automatically estimated in those regions in which absolute value pixel variation is above a specific threshold before and after the event;
   e) automatically estimated at an arbitrary position of a transducer;
   f) a weighted combination of said steps c), d) and e); and
   g) adjusted through a user interface.

9. The method according to claim 1, wherein said estimation of the temporal relationship among spatially remote signals of said image information of video sequences within a set of video sequences is computed at least by one of the following means selected from the group consisting of:

computing a model-based approach by means selected from the group consisting of a statistical parametric mapping (SPM), a cross-correlation analysis (CCA) or a coherence analysis (CA), and a predefined temporal model of local vessels; and computing a model-free approach by means selected from the group consisting of a modular graph decomposition, a principal component analysis, an independent component analysis, a clustering, a fuzzy clustering analysis and a hierarchical clustering analysis.

10. The method according to claim 2, wherein said specific risk factor of said living subject is further computed by integrating information of at least an additional second and different computed graph.

11. The method according to claim 2, further comprising:
computing said set of graph features by at least one of the following approaches selected from the group consisting of:
a standard graph analysis using one or more of the following criteria, clustering coefficient, path length, global efficiency, local efficiency, small-wordless, degree or degree distribution,
a spectral graph analysis using any of the following criteria, characteristic polynomial, eigenvalues, or eigenvectors;
a power graph analysis using any of the following criteria, decomposition of graph in power graphs and power nodes, minimal power graphs, power graph greedy algorithm or modular graph decomposition;
a hierarchical graph analysis using criteria selected from the group consisting of ordering by nested sets, hierarchical hidden Markov model, hierarchical clustering and hierarchical Bayes.

12. The method according to claim 2, wherein said predictive model of disease is selected from the group consisting of a computer model, a statistical model, a data model, a graphical model, a decision model or system model, a general linear model, a support vector machine regression model, a random forest, a decision tree, a generative model, and a discriminative model.

13. The method according to claim 2, wherein said specific risk factor from said predictive model of disease comprises using data information regarding said living subject, wherein said data information comprises using at least one of the following aspects selected from the group consisting of: biochemical, elastographic, imaging, clinical, genetic, epigenetic, protein expression or folding or current composite scores.

14. The method according to claim 2, wherein said specific risk factor from said predictive model of disease is computed by a complex biology system the input of which is done by parameters of the graph or graphs analysis selected from the group consisting of cellular automatons, a complex adaptive system, physiology simulators, models of vascular patterns or others.

15. The method according to claim 1, wherein said vascular networks are selected from the group consisting of being for monitoring patients with chronic liver diseases and cirrhosis of the liver, for diagnosing abnormal vascularization or tumors, and for monitoring of therapeutic effects for specific medical conditions selected from the group consisting of oncology, prognostic stratification of acute or a differentiation of healthy and abnormal tissue, and organs or body parts at risk of developing fibrosis.

16. The method according to claim 1, wherein said contrast-enhanced signals are selected from the group consisting of ultrasound, coherence tomography, fluorescence images, and magnetic resonance Imaging.

* * * * *